United States Patent
Schnier

(10) Patent No.: US 9,255,876 B2
(45) Date of Patent: Feb. 9, 2016

(54) TEMPERATURE SENSOR AND METHOD FOR MEASURING A TEMPERATURE CHANGE

(71) Applicant: Carl Zeiss SMS GmbH, Jena (DE)

(72) Inventor: Dietmar Schnier, Garbsen (DE)

(73) Assignee: Carl Zeiss SMS GmbH, Jena (DE)

( * ) Notice: Subject to any disclaimer, the term of this patent is extended or adjusted under 35 U.S.C. 154(b) by 0 days.

(21) Appl. No.: 13/844,362

(22) Filed: Mar. 15, 2013

(65) Prior Publication Data

US 2013/0258342 A1    Oct. 3, 2013

(30) Foreign Application Priority Data

Mar. 30, 2012    (DE) .................. 10 2012 006 420

(51) Int. Cl.
G01K 11/32    (2006.01)
G01J 3/45    (2006.01)
G01J 5/00    (2006.01)
G01N 21/17    (2006.01)

(52) U.S. Cl.
CPC ............... *G01N 21/171* (2013.01); *G01K 11/32* (2013.01)

(58) Field of Classification Search
CPC ........... G01K 13/00; G01K 11/32; G01J 5/08; G01J 3/45
USPC .............. 385/12, 14; 374/120, 130–132, 141, 374/161, 100, 43; 356/43, 450
See application file for complete search history.

(56) References Cited

U.S. PATENT DOCUMENTS

| 4,203,326 | A |   | 5/1980  | Gottlieb et al. |
|-----------|---|---|---------|------------------|
| 4,417,782 | A | * | 11/1983 | Clarke ...................... G01K 3/00 250/577 |
| 4,443,698 | A |   | 4/1984  | Schiffner |
| 4,515,430 | A | * | 5/1985  | Johnson ............................ 385/8 |
| 4,668,093 | A | * | 5/1987  | Cahill ................ G01D 5/35303 250/227.19 |
| 4,756,627 | A | * | 7/1988  | Nelson ........................... 374/159 |
| 5,306,162 | A | * | 4/1994  | Armendariz .................... 439/67 |
| 5,329,356 | A | * | 7/1994  | Tabarelli et al. ............... 356/498 |
| 5,349,437 | A | * | 9/1994  | Bobb ............................. 356/477 |
| 5,483,341 | A | * | 1/1996  | Naganuma ..................... 356/450 |
| 5,557,100 | A | * | 9/1996  | Jeuniaux et al. ......... 250/227.16 |
| 5,721,615 | A | * | 2/1998  | McBride et al. .............. 356/477 |

(Continued)

FOREIGN PATENT DOCUMENTS

| DE | 699 37 612 | 10/2008 | ............. G01K 11/32 |
| EP | 0 038 950 | 4/1981 | ............... G02B 5/14 |

(Continued)

OTHER PUBLICATIONS

Harrington, J.A., Infrared Fiber Optics, Feb. 2012, McGraw Hill, OSA Handbook, vol. III, pp. 1-13.*

(Continued)

*Primary Examiner* — Gail Kaplan Verbitsky
(74) *Attorney, Agent, or Firm* — Fish & Richardson P.C.

(57) ABSTRACT

A temperature sensor is provided which comprises a measurement light source for generating measurement light and two optical waveguides. The two optical waveguides are arranged such that they respectively receive a measurement light portion of the measurement light and that the measurement light portions are superimposed after passing through the optical waveguides. Furthermore, the two optical waveguides have an optical property with different temperature dependency.

20 Claims, 3 Drawing Sheets

(56) References Cited

U.S. PATENT DOCUMENTS

| | | | |
|---|---|---|---|
| 5,820,264 A * | 10/1998 | Tsao et al. | 374/131 |
| 6,018,390 A * | 1/2000 | Youmans | G01H 9/004 |
| | | | 250/227.19 |
| 6,024,488 A | 2/2000 | Wu et al. | |
| 6,137,573 A * | 10/2000 | Luke et al. | 356/453 |
| 6,266,141 B1 * | 7/2001 | Morita | 356/365 |
| 6,511,222 B1 * | 1/2003 | Bouamra | 374/161 |
| 6,535,290 B1 * | 3/2003 | Spanner et al. | 356/499 |
| 7,077,566 B2 * | 7/2006 | Rajendran et al. | 374/161 |
| 7,543,982 B2 * | 6/2009 | Yamamoto | G01B 11/18 |
| | | | 356/32 |
| 2002/0176088 A1 * | 11/2002 | Johnson et al. | 356/477 |
| 2003/0231690 A1 * | 12/2003 | McDonald | 372/97 |
| 2005/0121630 A1 * | 6/2005 | Arndt et al. | 250/504 R |
| 2005/0195401 A1 * | 9/2005 | Cao | G01J 9/0246 |
| | | | 356/454 |
| 2005/0271116 A1 * | 12/2005 | Ito | G01K 11/12 |
| | | | 374/120 |
| 2006/0204164 A1 * | 9/2006 | Ivtsenkov | 385/12 |
| 2006/0279743 A1 * | 12/2006 | Boesser et al. | 356/500 |
| 2006/0290937 A1 * | 12/2006 | Hirata et al. | 356/451 |
| 2008/0177482 A1 * | 7/2008 | Kishida et al. | 702/35 |
| 2009/0240455 A1 * | 9/2009 | Fromme | G01K 11/32 |
| | | | 702/85 |
| 2010/0134802 A1 * | 6/2010 | Chan et al. | 356/497 |
| 2011/0188047 A1 * | 8/2011 | Levy et al. | 356/477 |
| 2012/0241601 A1 * | 9/2012 | Kaufman | 250/282 |
| 2013/0301037 A1 * | 11/2013 | Handerek | G01D 5/353 |
| | | | 356/73.1 |
| 2013/0342902 A1 * | 12/2013 | Krueger et al. | 359/383 |
| 2014/0132962 A1 * | 5/2014 | Petschik et al. | 356/492 |

FOREIGN PATENT DOCUMENTS

| | | | |
|---|---|---|---|
| EP | 345188 A1 * | 12/1989 | |
| FR | 2 463 917 | 2/1981 | G01D 5/26 |

OTHER PUBLICATIONS

James A. Harrington, "Infrared Fiber Optics", (13 pages) downloaded on Feb. 15, 2012 under http://irfibers.rutgers.edu/resources/publications/2007/ir_fiber_review.pdf.

Peter L.M. Heydemann, "Determination and correction of quadrature fringe measurement errors in interferometers", *Applied Optics*, vol. 20, No. 19, Oct. 1, 1981, pp. 3382-3384.

Eric Pinet, Jochen Maier, "Faseroptische Fabry-Perot Sensoren", Laser Components GmbH, as published in SENSORS, Edition 1 of Oct. 2007, with English Translation.

* cited by examiner

TEMPERATURE SENSOR AND METHOD FOR MEASURING A TEMPERATURE CHANGE

CROSS-REFERENCE TO RELATED APPLICATION

This application claims priority to German Patent Application 10 2012 006 420.9, filed on Mar. 30, 2012. The entire disclosure of the above application is herein incorporated by reference.

BACKGROUND

The invention relates to a temperature sensor, a method for measuring a temperature change and a mask inspection apparatus for inspecting a lithography mask with this type of temperature sensor.

For highly accurate determination of the temperature of air for example with milli-Kelvin precision or better, in the prior art platinum temperature sensors are used. These platinum temperature sensors are used, for example, to stabilise the temperature in the region of the mask table of a mask inspection apparatus which is used for the inspection of a lithography mask. However, these platinum temperature sensors drift with several milli-Kelvin per year and react, moreover, to changes to the flow speed of the air surrounding them due to their self-heating. Sensors without any appreciable self-heating, e.g. capacitive length measuring systems, have not until now been able to demonstrate milli-Kelvin measuring accuracy.

SUMMARY

In one aspect, a temperature sensor and a method for measuring a temperature change are provided, such that highly accurate and stable temperature measurement in the long term is made possible, which is independent of environmental conditions such as pressure and airflows.

In one aspect, a temperature sensor which comprises a measurement light source for generating measurement light and two optical waveguides are provided. The optical waveguides are arranged such that they respectively receive a measurement light portion and that the measurement light portions are superimposed after passing through the optical waveguides. The two optical waveguides have an optical property with different temperature dependency.

In other words, the same optical property has a different temperature dependency for the two optical waveguides, i.e., the temperature dependency of the optical property of the first optical waveguide is different from the temperature dependency of the same optical property of the second optical waveguide. In particular, the temperature dependency of the optical property differs between the two optical waveguides by more than 10%, in particular by more than 50%, by more than the factor 2 or by more than the factor 5. The measurement light has a coherence length that is sufficiently long for the interference measurement. For this purpose the temperature sensor can have a suitable measurement light source, such as, e.g., a monochromatic frequency-stabilised laser for generating the measurement light.

As mentioned above, the optical waveguides are arranged such that they respectively receive a measurement light portion. For this purpose a light-splitting module, for example, in the form of a beam splitter can be provided. Alternatively however, the ends of the optical waveguides can also be arranged such that an irradiated beam illuminates both ends with the measurement light so that the measurement light penetrates into both optical waveguides. Furthermore, the optical waveguides are arranged such that the measurement light portions are superimposed after passing through the optical waveguides. For this purpose the temperature sensor can be provided, for example, with a light superimposition module. This light superimposition module can be identical to a light-splitting module of the aforementioned type or be in the form of a separate module. Alternatively, the measurement light portions can also be superimposed by the ends of the optical waveguides being arranged next to one another such that the latter jointly illuminate a detector surface, in particular at slightly different angles, and so the superimposition takes place on the detector surface.

Due to the use of optical waveguides with an optical property with different temperature dependency, the temperature sensor according to the invention enables a highly accurate temperature measurement. At the same time no appreciable aging effects, which would affect the accuracy of the temperature measurement, occur in the optical waveguides. Pressure fluctuations and airflows do not affect the temperature measurement either to any appreciable extent.

According to one embodiment the two optical waveguides are arranged within the same spatial measuring region. They are therefore subjected to the same temperature fluctuations.

According to a further embodiment of the invention the temperature sensor comprises more than two optical waveguides, in particular more than three or more than four optical waveguides, the optical property of which has a different temperature dependency for each pair. It is therefore possible to further increase the accuracy of the temperature measurement.

According to a further embodiment of the invention the optical property with different temperature dependency is the respective optical path length of the two optical waveguides. In this case, therefore, the optical waveguides are configured such that their respective optical path lengths have different temperature dependencies. According to one embodiment the temperature dependency difference between the optical path lengths of the two optical waveguides is greater than 1 μm per degree Kelvin temperature change, in particular greater than 5 μm or 10 μm per degree Kelvin temperature change.

According to a further embodiment of the invention, the two optical waveguides respectively have a light-conducting core and the two light-conducting cores are produced from different materials. According to an alternative embodiment the optical waveguides have different thicknesses. In other words, the temperature sensor comprises a first optical waveguide and a second optical waveguide with one light-conducting core respectively, and the material of the light-conducting core of the first optical waveguide differs from the material of the light-conducting core of the second optical waveguide.

According to one embodiment the temperature sensor further comprises a light-splitting module for splitting the incoming measurement light into the measurement light portions and the optical waveguides are respectively arranged at an outlet of the light-splitting module. Therefore, the optical waveguides respectively receive a measurement light portion of the measurement light. According to one embodiment the light-splitting module is an element separate from the optical waveguides. Thus, for example, a ground end surface of a glass fibre which brings about partial reflection of the light conveyed within the glass fibre is not considered in this connection to be a light-splitting module separate from the optical waveguides. The light-splitting module can, for example, be in the form of a beam splitter, in particular a polarising beam splitter, to which the optical waveguides are connected.

According to a further embodiment of the invention the measurement light source is configured to irradiate the measurement light in the form of a directed beam onto the two optical waveguides, the optical waveguides have respective input-side ends for receiving the measurement light portions and the input-side ends of the two optical waveguides are arranged so close to one another that the two input-side ends are captured by the beam of the measurement light. In particular, the measurement light source can be a laser. The latter generates a directed beam in the form of a laser beam. In order to ensure that the two input-side ends are captured by the beam of the measurement light, the ends can be arranged parallel to one another. In particular, they are arranged such that the ends are directly adjacent to one another. In this case, the ends can be connected to one another by means of a plug.

According to a further embodiment of the invention, the optical waveguides have respective output-side ends for the exit of the measurement light portions after passing through the optical waveguides, and the output-side ends are arranged so close to one another that after exiting from the optical waveguides the measurement light portions interfere with one another.

According to one embodiment of the invention, the material of one of the two light-conducting cores has a refractive index with a negative temperature dependency. In other words, the parameter dn/dT of this material is negative. According to one embodiment the material of one of the two light-conducting cores comprises ZBLAN. The material of the other of the two light-conducting cores can comprise e.g. quartz. Therefore, the use for example of a quartz monomode fibre can be considered.

According to a further embodiment of the invention the materials of the two light-conducting cores respectively have a temperature-dependent refractive index and respectively have a thermal expansion coefficient. With a specific temperature change on the one hand the temperature dependency of the refractive index and on the other hand a temperature dependency of a length expansion of the light-conducting cores determined by the expansion coefficients leads to a change in an optical path length difference between the two optical waveguides. The materials are configured such that the sum of the refractive index-dependent change in the optical path length and the expansion-dependent change in the optical path length for the two light-conducting cores produces different values. According to one embodiment the materials are configured such that the refractive index-dependent change in the optical path length difference outweighs the expansion-dependent change in the optical path length difference. In other words, the change in the optical path length difference between the path lengths through the two optical waveguides, which can be traced back to the temperature-dependent change of the refractive index of the respective light-conducting core, is greater than the change in the optical path length difference which can be traced back to the temperature-dependent expansion of the light-conducting cores of the optical waveguides.

According to a further embodiment of the invention, the two optical waveguides respectively have a length of at least 50 cm. According to further embodiments the two optical waveguides have a length of at least 1 m, at least 10 m or at least 100 m.

According to a further embodiment of the invention, the two optical waveguides are produced from flexible cables, in particular flexible fibre optic cables. It is therefore possible to arrange the optical waveguides within a closely defined measuring volume, for example by winding the cables.

According to a further embodiment of the invention, at least one of the two optical waveguides, preferably both optical waveguides, is in the form of a monomode fibre, in particular with a step index. According to an alternative embodiment, at least one of the two optical waveguides is in the form of a multimode fibre.

According to a further embodiment of the invention, the respective lengths of the two optical waveguides are matched to one another such that the optical path length through the two optical waveguides differs by less than 25%, in particular by less than 10%, less than 5%, less than 1% or less than 0.01%.

Furthermore, according to the invention a mask inspection apparatus for inspecting a lithography mask comprising a temperature sensor in any of the embodiments according to the invention described above is provided.

According to one embodiment the temperature sensor is located in the region of a mask table of the mask inspection apparatus.

Furthermore, according to the invention a position determining apparatus for determining the positioning of structures on a lithography mask (also called "registration measuring apparatus") which comprises a temperature sensor in any of the embodiments according to the invention described above is provided.

Furthermore, according to the invention a method for measuring a temperature change is provided. The method comprises the steps: arranging two optical waveguides such that they are subjected to the same temperature fluctuations, splitting incoming measurement light into two measurement light portions and introducing the measurement light portions into a respective one of the two optical waveguides, superimposing the two measurement light portions after passing through the optical waveguides, and recording a light intensity generated by the superimposition. Depending on the embodiment, the light intensity can be resolved locally and/or temporally. A locally resolved measurement can also be called the measurement of a light intensity distribution. According to one embodiment the light intensity recorded is evaluated in order to determine a temperature change. The temperature change determined relates to the temperature of the air surrounding the optical waveguides and/or of materials which are directly adjacent to optical waveguides.

According to one embodiment of the invention the two optical waveguides respectively have a light-conducting core and the two light-conducting cores are produced from different materials.

According to a further embodiment of the invention, the two optical waveguides are arranged such that they respectively have at least one twist. The twist can be formed such that at least one of the optical waveguides is in serpentine form or is also wound. This type of winding can be a circular winding or also a winding with a different type of geometry, e.g. an ellipsoidal or square geometry.

According to a further embodiment of the invention the two optical waveguides are respectively arranged with windings, the windings of the two optical waveguides running round a common axis. In other words, the windings of the optical waveguides are made such that the optical waveguides extend around the common axis. This does not necessarily mean, however, that the optical waveguides are arranged concentrically relative to the common axis. According to one embodiment at least one of the two optical waveguides has at least two windings, in particular at least five windings.

According to a further embodiment the method according to the invention is implemented using the temperature sensor in any of the embodiments according to the invention described above.

The features specified with regard to the embodiments of the method according to the invention listed above can be applied accordingly to the temperature sensor according to the invention. Conversely, the features specified with regard to the embodiments of the temperature sensor according to the invention listed above can be applied accordingly to the method according to the invention. These and other features of the embodiments according to the invention are described in the claims and in the description of the figures. The individual features can be realised either separately or in combination as embodiments of the invention. Furthermore, they can describe advantageous embodiments which can be protected independently and protection of the latter is optionally only claimed during or after pendency of the application.

BRIEF DESCRIPTION OF THE DRAWINGS

The above and further advantageous features of the invention are illustrated in the following detailed description of exemplary embodiments according to the invention with reference to the attached schematic drawings. These show as follows.

DETAILED DESCRIPTION

In the exemplary embodiments and embodiments described below, elements which are similar to one another functionally or structurally are provided as far as possible with the same or similar reference numbers. There, in order to understand the features of the individual elements of a specific exemplary embodiment one should refer to the description of other exemplary embodiments or to the general description of the invention.

Figure 1:
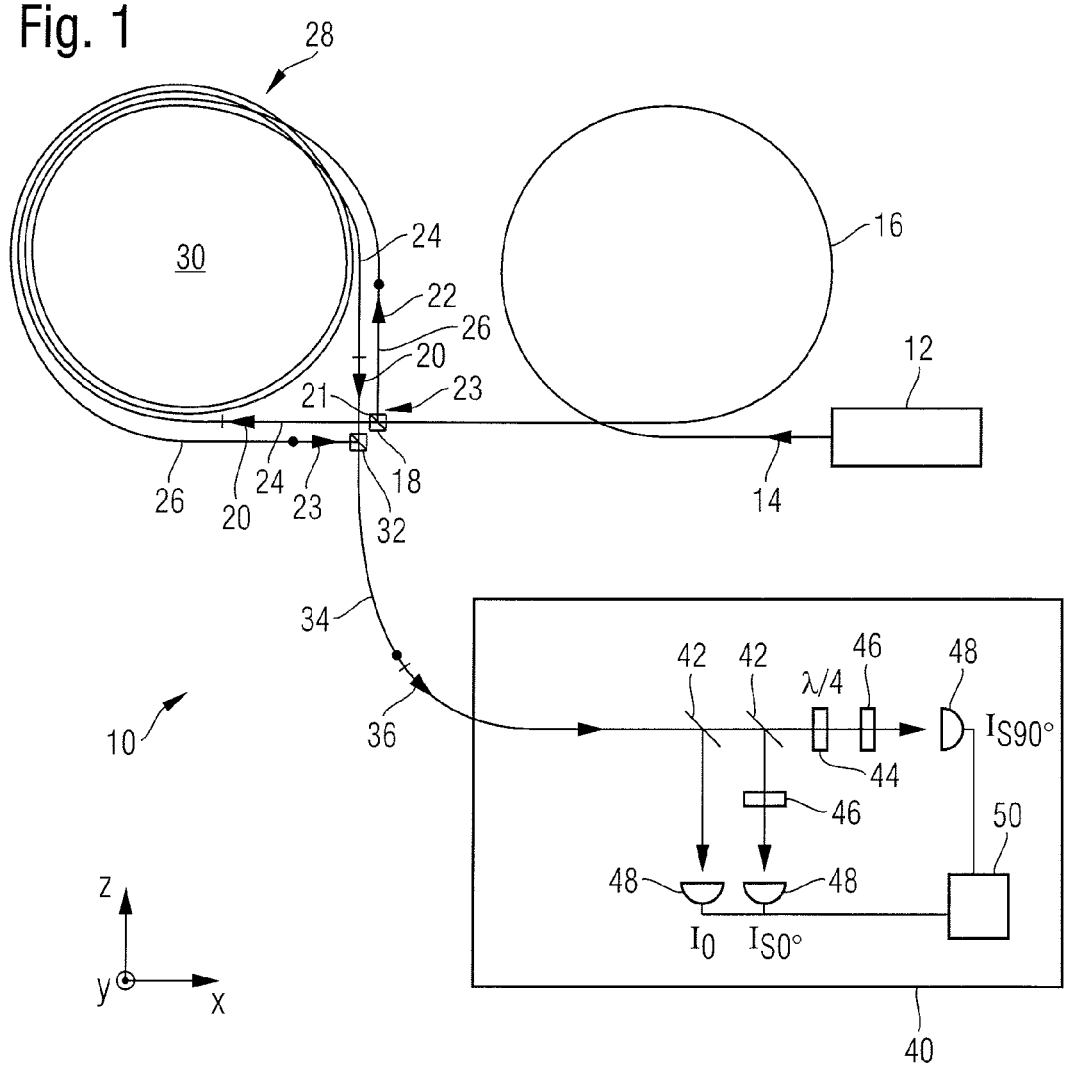
FIG. 1 a schematic illustration of a first embodiment of a temperature sensor according to the invention comprising two optical waveguides, FIG. 2 a schematic illustration of an exemplary structure of the optical waveguides according to FIG. 1, FIG. 3 a schematic illustration of a further embodiment of a temperature sensor according to the invention comprising two optical waveguides, FIG. 4 an illustration of an input-side region of the optical waveguides according to FIG. 3, FIG. 5 an illustration of radiation superimposition in an output-side region of the optical waveguides according to FIG. 3, and FIG. 6 a schematic illustration of a mask inspection apparatus for inspecting a lithography mask comprising the temperature sensor according to FIG. 1 or FIG. 3.

In order to facilitate the description of the projection exposure tool there is specified in the drawing a Cartesian xyz coordinate system which gives the respective relative position of the components shown in the figures. In FIG. 1 the y direction runs out of the plane of the drawing perpendicular to the latter, the x direction to the right, and the z direction upwards.

FIG. 1 illustrates an embodiment according to the invention of a temperature sensor 10 for measuring a temperature change in a medium, e.g. in air. The temperature sensor 10 comprises a measurement light source 12 for generating measurement light 14 with a coherence length that is sufficient for taking an interference measurement. The measurement light source 12 can comprise a laser, for example a helium-neon laser. In this case the wavelength of the measurement light 14 is approximately 633 nm and so comes within the visible wavelength range. Other wavelengths within the visible wavelength range or wavelengths within the UV wavelength range or within the infrared wavelength range are also conceivable.

The measurement light 14 is injected into a delivery waveguide 16 in the form of a glass fibre cable. The delivery waveguide 16 is connected by its exit-side end to an inlet 19 of a light-splitting module 18 in the form of a polarising beam splitter with fibre coupling. The measurement light 14 is split by the light-splitting module 18 into two measurement light portions polarised perpendicularly to one another, namely into a first measurement light portion 20 polarised parallel to the plane of the drawing according to FIG. 1 and into a second measurement light portion 22 polarised perpendicularly to the plane of the drawing. The light-splitting module 18 has two outlets 21 and 23 to which the two optical waveguides 24 and 26, respectively in the form of a glass fibre cable, are connected, namely such that the first measurement light portion 20 is injected into the first optical waveguide 24 and the second measurement light portion 22 is injected into the second optical waveguide 26. Polarisation-maintaining monomode fibres are particularly suitable as glass fibre cables. These guarantee outstanding stability with regard to movements and vibration.

The two optical waveguides 24 and 26 respectively have a number of windings, in the illustration of FIG. 1 these being respectively two windings, the windings of the two optical waveguides 24 and 26 having substantially the same winding axis and substantially the same winding radius. Therefore the optical waveguides 24 and 26 according to the embodiment shown form circular rings lying one over the other. These rings are arranged within a measuring region 30 for the temperature measurement.

The stability of the measurement signal depends essentially upon the mechanical stability of the optical waveguide behaviour. Therefore the optical waveguides 24 and 26 are preferably all laid stably and are fixed mechanically, for example by sticking or similar. It is thus ensured that no changes to the curvature radii of the optical waveguides 24 occur during the measurement which would lead to changes in the optical path length. The measuring region 30 for the temperature measurement can be kept relatively compact. The size of the measuring region 30 is determined by the minimum path radius of the glass fibre cables acting as optical waveguides 24 and 26.

The two optical waveguides 24 and 26 are connected by their respective exit-side end to a light superimposition module 32 in the form of a polarising beam splitter with fibre coupling. In the light superimposition module 32 the two measurement light portions 20 and 22 are interferometrically superimposed and introduced into a detection waveguide 34 in the form of a polarisation-maintaining glass fibre cable. The superimposed light in the detection waveguide 34 is referred to in the following as interference light 36. The interference light 36 is introduced by the detection waveguide 34 into a detection module 40.

In the detection module 40 the intensity $I_0$ of the interference light 36 is continuously measured chronologically. An evaluation unit 50 of the detection module 40 determines from a change in the intensity $I_0$ an underlying change to the path length difference between the optical path lengths in the first optical waveguide 24 and the second optical waveguide 26. From this in turn a temperature change at the location of the measuring region 30 is determined, as described in more detail below.

In the embodiment shown in FIG. 1, the detection module 40 is configured for homodyne laser interferometric measurement. For this purpose the detection module 40 has two partially reflective beam splitters 42, a λ/4 plate 44 and two polarisers 46. Part of the incoming interference light 36 is guided by a first beam splitter 42 onto a first intensity detector 48 in order to measure the intensity $I_0$. Part of the interference light 46 passing through the first beam splitter 42 is deflected by means of the second beam splitter 42, passes through a polariser 46 aligned in the 0° position and then strikes an intensity detector 48 which records the intensity $I_{S0°}$ of the interference light 36 with 0° polarisation direction. The part of the interference light passing through the second beam splitter 42 passes through the λ/4 plate 44 and a polariser aligned in the 90° polarisation direction before it strikes a further intensity detector 48 by means of which the intensity $I_{S90°}$ of the interference light 36 with the 90° polarisation direction is recorded.

The evaluation unit 50 also processes in addition to signal $I_0$ signals $I_{S0°}$ and $I_{S90°}$. Signals $I_{S0°}$ and $I_{S90°}$ make it possible to deduct cyclical errors, e.g. power fluctuations in the optical waveguides 24 and 26, tilts in the light-splitting module 18 and/or in the light superimposition module 32, as described e.g. in the document by P. L. M. Heydemann, "Determination and correction of quadrature fringe measurement errors in interferometers", Vol. 20, No. 19, October 1981, pages 3382-3384.

Alternatively to the homodyne detection method shown in FIG. 1, the use of a heterodyne detection method known to the person skilled in the art is also possible. In this case the measurement light 14 passing out of the measurement light source 12 has two components with different polarisation directions which have slightly different frequencies. A structure without polarisation-selective components is also possible if one uses a restricted measuring region with a path difference of +/−½π or generates a signal in a different form that enables unambiguous determination of the algebraic sign of the path difference.

Figure 2:
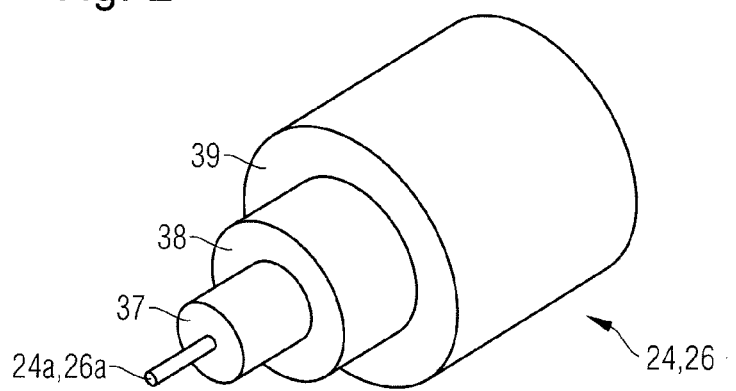

FIG. 2 schematically illustrates the structure of the optical waveguides 24 and 26. The latter have a step index profile. Each of the optical waveguides comprises a light-conducting core 24a or 26a, a jacket 37 surrounding the light-conducting core, a protective coating 38 surrounding the jacket 37 and an outer casing 39 surrounding the protective coating 38. According to one embodiment the core 24a or 26a has a diameter of 2 μm to 10 μm. The core 24a or 26a and the respective jacket 37 are typically produced from the same glass with different doping so that the refractive index $n_K$ of the core is greater than the refractive index $n_M$ of the jacket.

The material of the light-conducting core 24a of the first optical waveguide 24 differs from the material of the light-conducting core 26a of the second optical waveguide 26. The first optical waveguide 24 is in the form of a quartz monomode fibre. The second optical waveguide 26 comprises a non-doped ZBLAN monomode fibre. The light-conducting core 24a of the first optical waveguide 24 is therefore made of quartz glass, while that of the light-conducting core 26a of the second optical waveguide 26 is made of the fluoride glass ZBLAN. The optical waveguide 24 and/or the optical waveguide 26 can alternatively also be made of multimode fibres instead of monomode fibres.

ZBLAN stands for the composition $ZrF_4$—$BaF_2$—$LaF_3$-$AlF_3$—$NaF$ and in contrast to quartz glass has a negative temperature dependency dn/dT of the refractive index, as illustrated by the table below:

| Material | Refractive index n | dn/dT [$10^{-6}$/° C.] | Thermal expansion coefficient α [$10^{-6}$/° C.] |
|---|---|---|---|
| Quartz glass | 1.455 | 12 | 0.55 |
| ZBLAN | 1.499 | −15 | 17.2 |

According to one embodiment the optical waveguides 24 and 26 of the temperature sensor 10 shown in FIG. 1 respectively have a length of 1.0 m. A temperature change at the location of the measuring region 30 of +1 K leads to the following changes $dL_1$ and $dL_2$ in the optical path length of the two optical waveguides 24 and 26:

optical waveguide 24 (quartz glass): $dL_1 = (12+0.55) \cdot 10^{-6}$ m $= 12.55 \cdot 10^{-6}$ m optical waveguide 26 (ZBLAN): $dL_2 = (-15+17.2) \cdot 10^{-6}$ m $= 2.2 \cdot 10^{-6}$ m Therefore, for a change $d(\Delta L)$ of the path length difference between the two optical waveguides 24 and 26 a value of 10.35 μm per degree Kelvin temperature change is given. If one divides the change $d(\Delta L)$ in the path length difference into a refractive index-dependent portion $d(\Delta L_n)$ and an expansion-dependent portion $d(\Delta L_\alpha)$, the following values are given: $d(\Delta L_n) = 27$ μm/K and $d(\Delta L_\alpha) = -16.65$ μm/K. The value of the refractive index-dependent portion $d(\Delta L_n)$ is greater than the value of the expansion-dependent portion $d(\Delta L_\alpha)$, and so the refractive index-dependent change in the optical path length difference outweighs the expansion-dependent change in the optical path length difference.

As mentioned above, with an optical waveguide length of 1.0 m a path length difference of approximately 10 μm, also called path difference, occurs per degree Kelvin temperature change. With the detection module 40 described above, a thousandth of this value can by all means be detected. Therefore, in the aforementioned embodiment measurement resolutions of 1 mK or better can be achieved. In further embodiments the optical waveguides 24 and 26 have longer dimensions, for example having a length of 10 m or 100 m, by means of which the temperature resolution is correspondingly increased.

Figure 3:
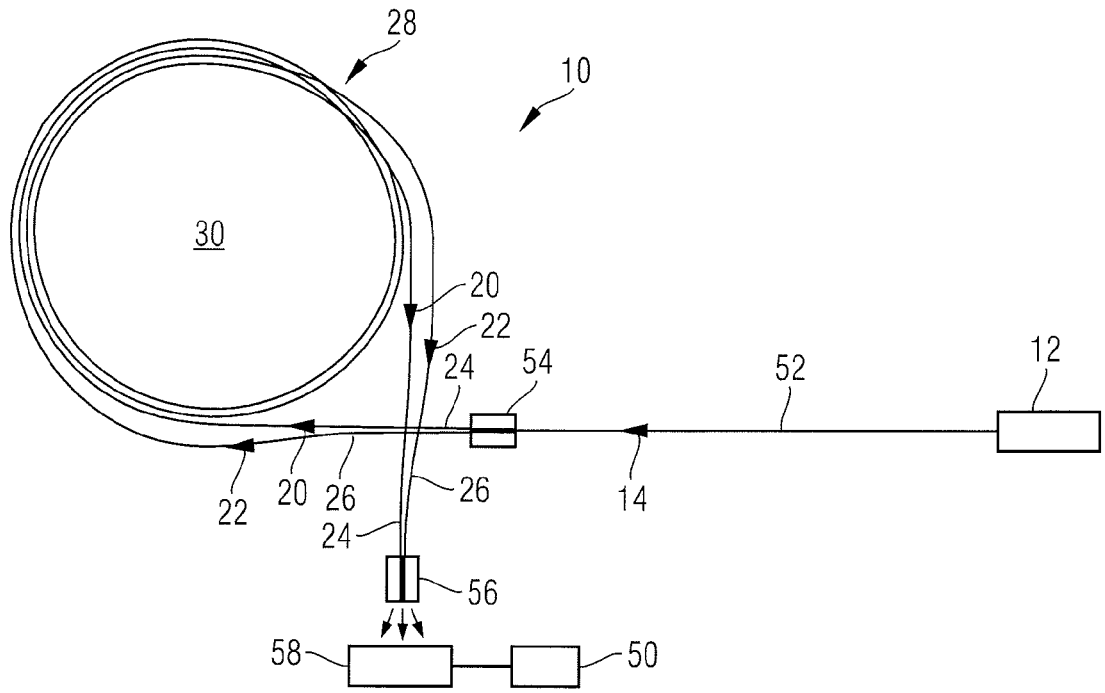

FIG. 3 shows a further embodiment according to the invention of a temperature sensor 10. Like the temperature sensor 10 according to FIG. 1, this sensor has two optical waveguides 24 and 26 which are in the form described with regard to FIG. 1. Unlike the temperature sensor 10 according to FIG. 1, in the embodiment according to FIG. 3 the measurement light 14 generated by a measurement light source 12 in the form of a laser, for example a helium-neon laser, is not delivered by means of a delivery waveguide 16 to the optical waveguides 24 and 26. Rather, the measurement light 14 is irradiated as a directed beam 52 onto an inlet plug 54 of the temperature sensor 10 according to FIG. 3.

Figure 4:
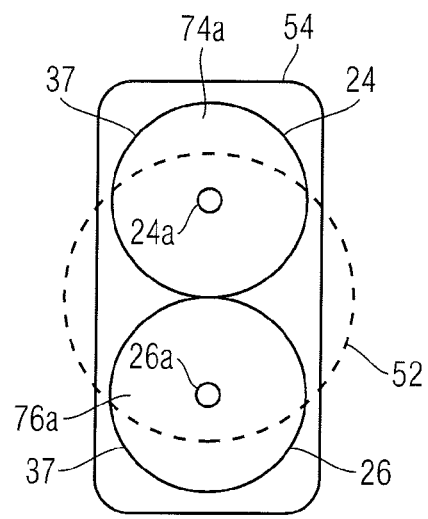

The inlet plug 54 connects the two optical waveguides 24 and 26. The structure of the inlet plug 54 is shown in FIG. 2. The end of the inlet plug 54 facing towards the measurement light source 12 is shown schematically in a top view in FIG. 4. As can be seen from the illustration, in the region of the inlet plug 54 the protective coating 38 and the outer casing 39 of the optical waveguides 24 and 26 are respectively removed, i.e. on their input-side ends 74a and 76a the optical waveguides 24 and 26 only have their respective light-conducting core 24a or 26a and their respective jacket 37. The optical waveguides 24 and 26 are arranged directly adjacent to one another in the inlet plug 24 so that their jackets 37 touch.

According to one embodiment the two cores 24a and 26a are 125 μm apart in the inlet plug 54. This distance is so small that the irradiated directed beam 52 of the helium-neon laser, which typically has a diameter of between 0.5 mm and 1.0 mm, illuminates both cores 24a with a light intensity that is so high that sufficient measurement light 52 passes into the two input-side ends 74a and 76a of the optical waveguides 24 and 26. The measurement light that has passed into the first optical waveguide 24 is called the first measurement light portion 20, while the measurement light that has passed into the second optical waveguide 26 is called the second measurement light portion 22.

The two measurement light portions 20 and 22 then pass through the corresponding optical waveguides 24 and 26 and pass out on the output-side ends 74b and 76b of the optical waveguides 24 and 26. Analogously to the input-side ends 74a and 76a, the output-side ends 74b and 76b are enclosed within a plug, a so-called outlet plug 56. In the region of the outlet plug 56 the protective coating 38 and the outer casing 39 of the optical waveguides 24 and 26 are also respectively removed, and the jackets 37 of the two optical waveguides 24 and 26 are adjacent to one another, as shown in FIG. 5.

Furthermore, the temperature sensor 10 according to FIG. 3 comprises a two-dimensionally resolving detector 58, such as for example a diode line or a CCD/CMOS sensor. The latter is a certain distance, for example approximately 5 cm, away from the outlet plug 56 so that the measurement light portions 20 and 22 passing out of the output-side ends 74b and 76b are superimposed on the detection surface of the detector 58 and so interfere with one another. The interference produces a stripe pattern 60 on the detection surface which is recorded by the detector 58.

Figure 5:
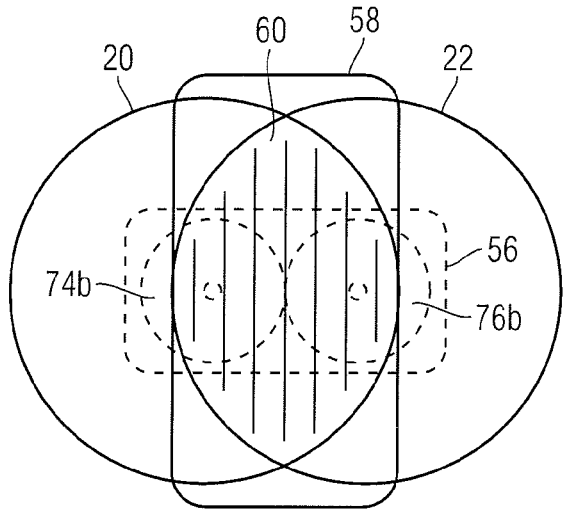

FIG. 5 illustrates the stripe pattern 60 produced by the superimposition of the measurement light portions 20 and 22 on the detector 58. A temperature change at the location of the measuring region 30 leads to a lateral shift of the stripe pattern with a clearly defined algebraic sign. An evaluation unit 50 determines a temperature change at the location of the measuring region 30 from the stripe pattern 60 recorded.

Figure 6:
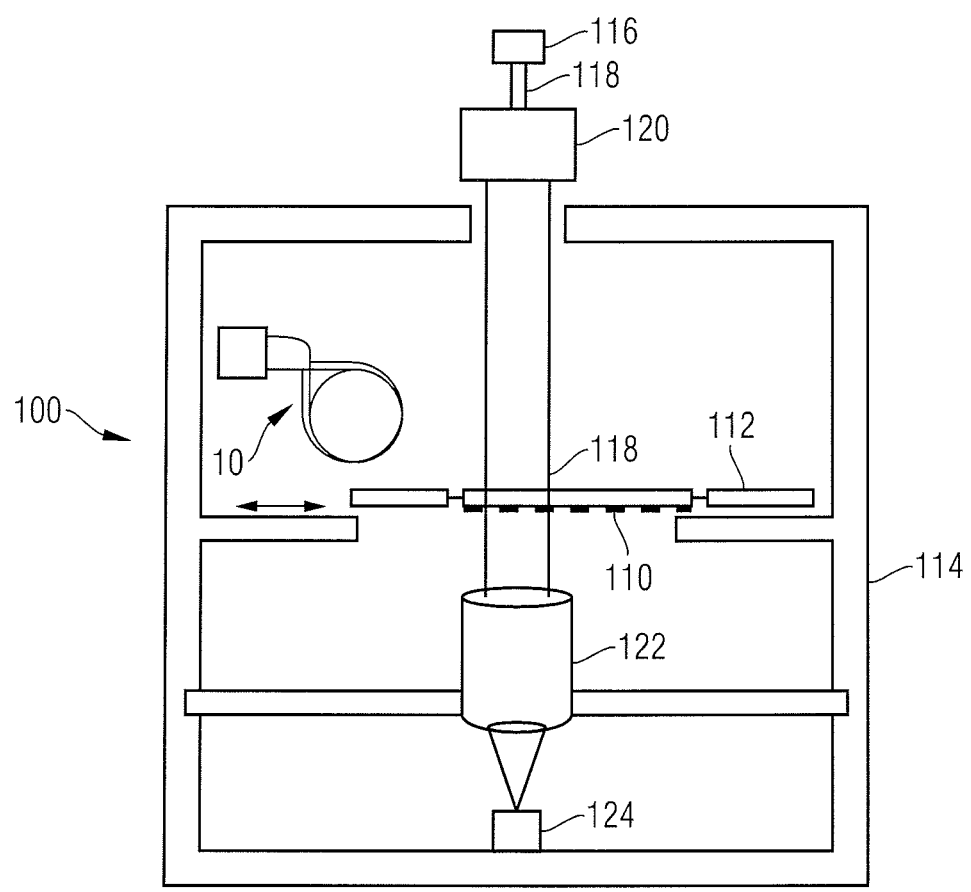

FIG. 6 illustrates a possible use for the temperature sensor 10 described above according to FIG. 1 or FIG. 3 in a mask inspection apparatus 100 for inspecting a lithography mask 110. This type of mask inspection apparatus 100 is used to measure the aerial image of the lithography mask 110 outside of a projection exposure tool in order to identify writing errors of the mask. The mask inspection apparatus 100 comprises an inspection light source 116 for generating inspection radiation 118. The wavelength of the inspection radiation 118 corresponds to the wavelength for which the lithography mask 110 is configured for use in a projection exposure tool. The wavelength of the inspection radiation 118 can for example be within the DUV wavelength range, e.g. 248 nm or 193 nm, or also be within the EUV wavelength range. The inspection radiation 118 is irradiated onto the lithography mask 110 by means of an illumination system 120. The lithography mask 110 is then imaged onto a detector 124 by means of imaging optics 122. The lithography mask 110 is held by a mask holder in the form of a mask table 112 here.

During the inspection the mask table 112 is shifted step by step transversely to the optical axis of the imaging optics 122 relative to a frame 114 of the mask inspection apparatus 100. The air volume in the region of the mask table 112 is temperature-stabilised during operation of the mask inspection apparatus 100. For this purpose, in one of the embodiments described above, the temperature sensor 10 is disposed above or below the mask table 112. The air temperature can be measured with mK accuracy by the temperature sensor 10 according to the invention despite the airflows occurring here due to the movement of the mask table 112. The measurement result is used to control a heating and/or cooling device in the region of the mask table 112.

The temperature sensor 10 according to FIG. 1 or FIG. 3 can also be used in a position determining apparatus in the form of a so-called "registration measuring apparatus". This position determining apparatus determines the exact positioning of lithography structures on the lithography mask 100 in relation to target positionings. The basic structure of this type of position determining apparatus corresponds to the structure of the mask inspection apparatus 100 shown in FIG. 6. According to one embodiment the temperature sensor is also disposed above or below the mask table 112.

A temperature sensor according to an exemplary comparison comprises two identical optical waveguides. Therefore the two optical waveguides have the same temperature dependency. This type of temperature sensor can also be used in a mask inspection apparatus or a position determining apparatus. Here, one of the optical waveguides is located at a measuring location e.g. above or below the mask table. The other optical waveguide is disposed at a different location, the temperature of which is known and is as stable as possible. This location serves as the reference location and can for example comprise a reservoir with icy water. In this arrangement the temperature sensor takes a comparison measurement between the temperatures at the measuring location and at the reference location.

A number of implementations have been described. Nevertheless, it will be understood that various modifications may be made. For example, elements of one or more implementations may be combined, deleted, modified, or supplemented to form further implementations. In addition, other components may be added to, or removed from, the described temperature sensors. Accordingly, other implementations are within the scope of the following claims.

What is claimed:

1. A temperature sensor comprising:
   a measurement light source for generating measurement light; and
   two optical waveguides, the two optical waveguides being arranged such that they respectively receive a measurement light portion of the measurement light and that the measurement light portions are superimposed after passing through the optical waveguides, and the two optical waveguides having an optical property with different temperature dependency,
   wherein the optical waveguides have respective output-side ends for the exit of the measurement light portions after passing through the optical waveguides and the output-side ends are arranged so close to one another that after exiting from the optical waveguides the measurement light portions interfere with one another to generate a stripe pattern on a detection surface, wherein the stripe pattern is indicative of the temperature sensed by the sensor.

2. The temperature sensor according to claim 1, wherein the optical property with different temperature dependency is the respective optical path length of the two optical waveguides.

3. The temperature sensor according to claim 1, wherein the two optical waveguides respectively have a light-conducting core and the two light-conducting cores are produced from different materials.

4. The temperature sensor according to claim 1, further comprising a light-splitting module for splitting the incoming measurement light into the measurement light portions and wherein the optical waveguides are respectively arranged at an outlet of the light-splitting module.

5. The temperature sensor according to claim 1, wherein the measurement light source is configured to irradiate the measurement light in the form of a directed beam onto the two optical waveguides, the optical waveguides have respective input-side ends for receiving the measurement light portions and the input-side ends of the two optical waveguides are arranged so close to one another that the two input-side ends are captured by the beam of the measurement light.

6. The temperature sensor according to claim 3, wherein the material of one of the two light-conducting cores has a refractive index with a negative temperature dependency.

7. The temperature sensor according to claim 3, wherein the material of one of the two light-conducting cores comprises ZBLAN.

8. The temperature sensor according to claim 3, wherein the materials of the two light-conducting cores respectively have a temperature-dependent refractive index and respectively have a thermal expansion coefficient such that with a specific temperature change, the temperature dependency of the refractive index and a temperature dependency of a length expansion of the light-conducting cores determined by the expansion coefficients lead to a change in an optical path length difference between the two optical waveguides, wherein the refractive index-dependent change in the optical path length difference outweighs the expansion-dependent change in the optical path length difference.

9. The temperature sensor according to claim 1, wherein the two optical waveguides respectively have a length of at least 50 cm.

10. The temperature sensor according to claim 1, wherein the two optical waveguides are produced from flexible cables.

11. The temperature sensor according to claim 1, wherein at least one of the two optical waveguides is in the form of a monomode fibre.

12. The temperature sensor according to claim 1, wherein the respective lengths of the two optical waveguides are matched to one another such that the optical path length through the two optical waveguides differs by less than 10%.

13. A mask inspection apparatus for inspecting a lithography mask comprising a temperature sensor according to claim 1.

14. A position determining apparatus for determining the positioning of structures on a lithography mask comprising a temperature sensor according to claim 1.

15. A method for measuring a temperature change comprising:
arranging two optical waveguides such that they are subjected to the same temperature fluctuations;
generating measurement light and introducing one respective measurement light portion of the measurement light into each of the two optical waveguides;
superimposing the two measurement light portions after passing through the optical waveguides; and
recording a light intensity generated by the superimposition,
wherein the optical waveguides have respective output-side ends for the exit of the measurement light portions after passing through the optical waveguides and the output-side ends are arranged so close to one another that after exiting from the optical waveguides the measurement light portions interfere with one another to generate a stripe pattern on a detection surface, wherein the stripe pattern is indicative of the temperature sensed by the sensor.

16. The method according to claim 15, wherein the two optical waveguides respectively have an optical property with different temperature dependency.

17. The method according to claim 15, wherein the two optical waveguides are arranged such that they respectively have at least one twist.

18. The method according to claim 15, wherein the two optical waveguides are respectively arranged with windings, the windings of the two optical waveguides running round a common axis.

19. The method according to claim 15, which is implemented using a temperature sensor comprising a measurement light source for generating measurement light and two optical waveguides, the two optical waveguides being arranged such that they respectively receive a measurement light portion of the measurement light and that the measurement light portions are superimposed after passing through the optical waveguides, and the two optical waveguides having an optical property with different temperature dependency.

20. A temperature sensor comprising:
a measurement light source for generating measurement light; and
two optical waveguides, the two optical waveguides being arranged such that they respectively receive a measurement light portion of the measurement light and that the measurement light portions are superimposed after passing through the optical waveguides, and the two optical waveguides having an optical property with different temperature dependency,
wherein the optical waveguides have respective output-side ends for the exit of the measurement light portions after passing through the optical waveguides and the output-side ends are arranged so close to one another that after exiting from the optical waveguides the measurement light portions interfere with one another in a region that does not have a waveguide, wherein the measurement light portions interference is indicative of the temperature sensed by the sensor.

* * * * *